US012782272B2

(12) United States Patent
Strasfeld

(10) Patent No.: US 12,782,272 B2
(45) Date of Patent: Nov. 3, 2026

(54) MULTISPECTRAL SAMPLE ANALYSIS USING ABSORPTION SIGNATURES

(71) Applicant: Precision Healing LLC, Newton, MA (US)

(72) Inventor: David B Strasfeld, Somerville, MA (US)

(73) Assignee: Precision Healing LLC, Newton, MA (US)

( * ) Notice: Subject to any disclaimer, the term of this patent is extended or adjusted under 35 U.S.C. 154(b) by 1172 days.

(21) Appl. No.: 17/564,318

(22) Filed: Dec. 29, 2021

(65) Prior Publication Data

US 2022/0120676 A1 Apr. 21, 2022

Related U.S. Application Data

(63) Continuation-in-part of application No. 17/155,141, filed on Jan. 22, 2021, now Pat. No. 12,053,262.

(Continued)

(51) Int. Cl.
*G01N 21/31* (2006.01)
*A61B 5/00* (2006.01)
*G16H 20/40* (2018.01)

(52) U.S. Cl.
CPC ......... *G01N 21/3103* (2013.01); *A61B 5/445* (2013.01); *G16H 20/40* (2018.01); *A61B 5/0077* (2013.01); *G01N 2201/068* (2013.01)

(58) Field of Classification Search
CPC ......... G01N 21/3103; G01N 2201/068; G01N 2021/6417; G01N 2021/6421;

(Continued)

(56) References Cited

U.S. PATENT DOCUMENTS 5,553,616 A * 9/1996 Ham ...................... G01N 21/65 250/341.1
5,701,902 A * 12/1997 Vari ..................... A61B 5/0059 600/476

(Continued)

OTHER PUBLICATIONS

International Search Report dated May 6, 2021 for PCT/US2021/014501.

(Continued)

*Primary Examiner* — Sanjay Cattungal
(74) *Attorney, Agent, or Firm* — Adams Intellex, PLC

(57) ABSTRACT

Disclosed techniques include multispectral sample analysis using absorption signatures. At least two excitation light wavelengths are provided to a material sample. The sample exhibits absorption characteristics along the Red-Green-Blue (RGB) light wavelength spectrum. Output values of an RGB sensor are measured. The measuring detects the absorption characteristics of the sample. The absorption characteristics are in response to the at least two excitation light wavelengths. A third excitation light wavelength is provided and an additional output value of the RGB sensor is measured. The providing at least two excitation light wavelengths and a third excitation light wavelength enable water identification and biochrome identification. An indication of composition of the material sample is generated. The indication is based on interpreting the output values that were measured. An additional RGB sensor enables stereoscopic sensor imaging.

28 Claims, 7 Drawing Sheets

Related U.S. Application Data

(60) Provisional application No. 63/132,541, filed on Dec. 31, 2020, provisional application No. 62/964,969, filed on Jan. 23, 2020.

(58) Field of Classification Search
CPC .... G01N 21/645; G01N 21/251; A61B 5/445; A61B 5/0077; A61B 5/0071; A61B 5/0075; A61B 5/1032; A61B 5/441; A61B 5/443; G16H 20/40; G16H 10/40; G16H 30/40; G16H 50/20; Y02A 90/10
See application file for complete search history.

(56) References Cited

U.S. PATENT DOCUMENTS

| | | | | |
|---|---|---|---|---|
| 5,784,162 | A * | 7/1998 | Cabib | G01J 3/453 435/6.12 |
| 6,205,354 | B1 * | 3/2001 | Gellermann | A61B 5/1455 356/301 |
| 6,998,247 | B2 * | 2/2006 | Monfre | G01N 21/359 435/14 |
| 8,025,851 | B2 | 9/2011 | Slowey et al. | |
| 8,385,615 | B2 * | 2/2013 | Levenson | G01N 21/6486 600/407 |
| 8,634,607 | B2 * | 1/2014 | Levenson | G01N 21/6456 600/475 |
| 10,146,912 | B2 | 12/2018 | Drysdale et al. | |
| 10,299,965 | B1 | 5/2019 | Brar | |
| 10,376,148 | B2 | 8/2019 | Wood et al. | |
| 10,438,356 | B2 | 10/2019 | Dacosta | |
| 10,517,483 | B2 | 12/2019 | Wood et al. | |
| 10,618,983 | B2 | 4/2020 | Mitragotri et al. | |
| 10,783,632 | B2 | 9/2020 | Fan et al. | |
| 2002/0016534 | A1 * | 2/2002 | Trepagnier | A61B 5/0062 600/316 |
| 2002/0082487 | A1 * | 6/2002 | Kollias | A61B 5/1455 600/316 |
| 2002/0091324 | A1 * | 7/2002 | Kollias | A61B 5/0071 600/476 |
| 2005/0131304 | A1 * | 6/2005 | Stamatas | G01N 21/64 600/476 |
| 2006/0092315 | A1 * | 5/2006 | Payonk | A61B 5/445 348/370 |
| 2007/0173725 | A1 | 7/2007 | Souta et al. | |
| 2007/0265532 | A1 * | 11/2007 | Maynard | A61B 5/14532 600/477 |
| 2007/0276199 | A1 * | 11/2007 | Ediger | A61B 5/0071 600/300 |
| 2008/0076985 | A1 * | 3/2008 | Matousek | A61B 5/0075 600/310 |
| 2008/0214460 | A1 | 9/2008 | Neuberger et al. | |
| 2009/0137908 | A1 * | 5/2009 | Patwardhan | A61B 5/444 600/476 |
| 2009/0162423 | A1 | 6/2009 | Neuberger et al. | |
| 2010/0168586 | A1 * | 7/2010 | Hillman | A61B 5/0064 348/E13.001 |
| 2011/0021973 | A1 | 1/2011 | Neuberger et al. | |
| 2011/0039342 | A1 | 2/2011 | Percival et al. | |
| 2012/0268573 | A1 * | 10/2012 | Schonborn | A61B 5/0062 348/E13.074 |
| 2013/0053677 | A1 | 2/2013 | Schoenfeld | |
| 2014/0163389 | A1 | 6/2014 | Kudenov et al. | |
| 2015/0287191 | A1 * | 10/2015 | Koruga | A61B 5/444 382/128 |
| 2016/0030132 | A1 | 2/2016 | Cheung et al. | |
| 2016/0157725 | A1 * | 6/2016 | Munoz | H04N 23/51 600/407 |
| 2016/0166194 | A1 | 6/2016 | Gareau et al. | |
| 2017/0160189 | A1 | 6/2017 | Priore | |
| 2018/0202927 | A1 | 7/2018 | Isikman et al. | |
| 2019/0133502 | A1 | 5/2019 | Gomi et al. | |
| 2020/0104998 | A1 * | 4/2020 | Dacosta | A61B 5/445 |

OTHER PUBLICATIONS

Niu, L., Zhao, F., Chen, J., Nong, J., Wang, C., Wang, J., . . . & Hu, S. (2018). Isothermal amplification and rapid detection of Klebsiella pneumoniae based on the multiple cross displacement amplification (MCDA) and gold nanoparticle lateral flow biosensor (LFB). Plos one, 13(10), e0204332.

* cited by examiner

MULTISPECTRAL SAMPLE ANALYSIS USING ABSORPTION SIGNATURES

RELATED APPLICATIONS

This application claims the benefit of U.S. provisional patent application "Multispectral Sample Analysis Using Fluorescence Signatures" Ser. No. 63/132,541, filed Dec. 31, 2020.

This application is also a continuation-in-part of U.S. patent application "Skin Diagnostics Using Optical Signatures" Ser. No. 17/155,141, filed Jan. 22, 2021, which claims the benefit of U.S. provisional patent applications "Systems and Methods for Wound Care Diagnostics and Treatment" Ser. No. 62/964,969, filed Jan. 23, 2020, and "Multispectral Sample Analysis Using Fluorescence Signatures" Ser. No. 63/132,541, filed Dec. 31, 2020.

Each of the foregoing applications is hereby incorporated by reference in its entirety.

FIELD OF ART

This application relates generally to sample analysis and more particularly to multispectral sample analysis using absorption signatures.

BACKGROUND

Materials, whether natural or manufactured ones, are indispensable to the lives of people everywhere. People wear items of clothing of various materials to cover or protect, and to keep cool or warm. Clothing is also worn to make statements about class, culture, origin, and beliefs. People live in temporary or permanent structures depending on purpose, design, and materials used. People travel on or in vehicles manufactured from materials. A given object can be formed from materials based on a substance or a mixture of substances. Often used materials include woods, plastics, metals, fabrics, and glass. The materials can be used in their natural forms or can be combined with other materials to form compounds, composites, alloys, or blends. The constituents of a material or combination of materials can be identified by studying various properties. The properties can include material hardness, visual appearance, and weight; physical properties such as state, where the material state includes solid, liquid, gas, or plasma; and other physical properties such as density and magnetic characteristics of the material. The material properties can include chemical properties such as chemical resistance and combustibility. The material properties can include mechanical properties such as malleability, ductility, and strength; and electrical properties such as conductivity and resistivity. The properties of a material can include optical properties such as transmissivity and absorptivity. Because each material has its own unique set of properties, the physical, chemical, mechanical, electrical, optical, and other responses of a material can be analyzed to characterize and identify unknown materials.

Analysis and characterization of materials are widely applied in many industries including manufacturing, aerospace, and taxonomy, to name but a few. The analysis and characterization of materials is also widely utilized in research applications to identify a material or materials within a sample, to characterize new alloys or compounds of materials, and so on. The analysis and characterization of materials can also be used to identify the presence of unexpected materials within a sample. Some applications include identifying contaminants or impurities within materials, where the contaminants cause systems made from the materials to fail. Sophisticated testing procedures and advanced testing techniques can provide detailed information about a material. The detailed information can include identification of the chemical composition of the material. This latter class of analysis based on cutting edge procedures and techniques can require complex laboratory equipment and advanced training. For example, surface topology and composition of a material can be determined using a scanning electron microscope (SEM), which uses a beam of electrons, while a transmission electron microscope (TEM) can be used in crystalline defect analysis to predict behavior and to find failure mechanisms for materials. Also, X-ray Diffraction (XRD) is used to identify and characterize crystalline materials. These complicated and expensive tests, techniques, and types of equipment, usually available only in laboratories, can be used alone or in combination to characterize and identify unknown materials.

SUMMARY

Techniques for characterizing and identifying materials using multispectral sample analysis based on absorption signatures are disclosed. The absorption signatures can be based on light along the red-green-blue (RGB) light wavelength spectrum. This technique uses light from a range of wavelengths across the electromagnetic spectrum to determine light absorption by a material. The absorption characteristics are in response to at least two excitation light wavelengths. A light source is absorbed by molecules of a compound, causing little or no light from the light source to be reflected by the compound. The lack of reflected light from the light source by the material can be detected by one or more RGB sensors. The RGB sensors can be components of a broad-spectrum image sensor. The broad-spectrum sensor can employ an integrated, very low-cost Bayer filter, which enables the broad-spectrum image sensor to provide sensitivities to particular wavelengths, including light from frequencies which are visible to the human eye and those which are not. Various materials absorb different wavelengths of light when compared to one another. However, multispectral imaging can be used to differentiate materials based on their spectral absorption signatures and their absorption characteristics. As disclosed, multispectral absorption imaging can reduce the complexity, cost, and deployment challenges of using specialized multispectral cameras, elaborate optical filters, and expensive filter wheels which have orientation and alignment sensitivities, and employing fixed, lab-only equipment placement. The providing of excitation light wavelengths and the measuring output values of one or more RGB sensors can be performed by a mobile, outdoor-suitable vehicle. The mobile, outdoor-suitable vehicle can include a drone aircraft, an autonomous vehicle, and so on.

A method for multispectral sample analysis is disclosed comprising: providing at least two excitation light wavelengths to a material sample, wherein the material sample exhibits absorption characteristics along the Red-Green-Blue (RGB) light wavelength spectrum; measuring output values of an RGB sensor, wherein the measuring detects the absorption characteristics of the material sample, and wherein the absorption characteristics are in response to the at least two excitation light wavelengths; and generating an indication of composition of the material sample, wherein the indication is based on interpreting the output values that were measured. Embodiments include providing a third excitation light wavelength and measuring an additional output value of the RGB sensor. The at least two excitation light wavelengths and the third excitation light wavelength are at least 100 nm apart from each other. The providing at least two excitation light wavelengths and the providing a third excitation light wavelength enable water identification. The water identification comprises identifying a predominately monotonically increasing absorption at longer wavelengths. The providing at least two excitation light wavelengths and the providing a third excitation light wavelength enables biochrome identification.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
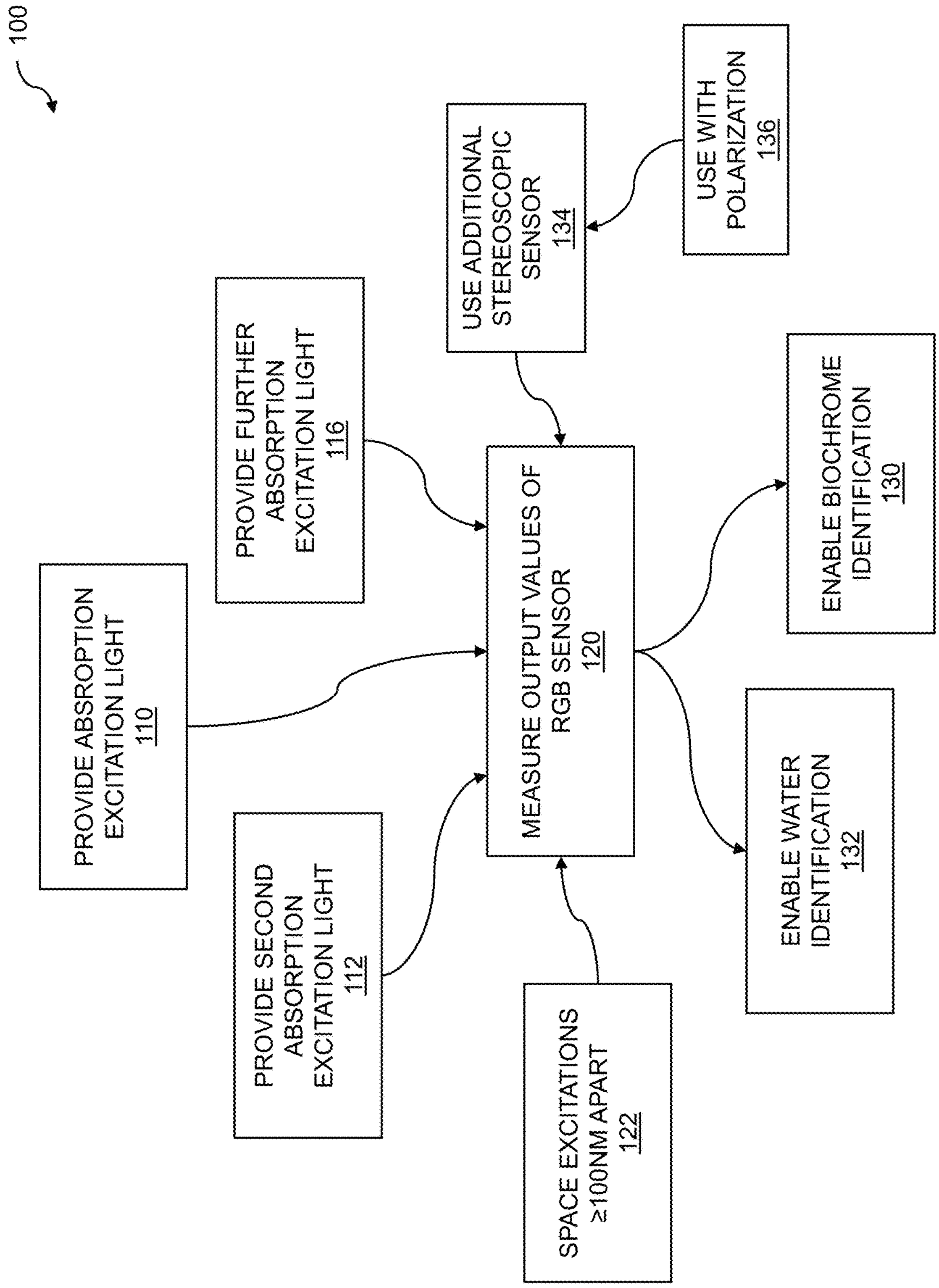
FIG. 1 is a flow diagram for multispectral sample analysis using absorption signatures.

Techniques for characterizing and identifying materials using multispectral sample analysis based on absorption signatures are disclosed. The absorption signatures can be based on light along the Red-Green-Blue (RGB) light wavelength spectrum. This technique uses light from a range of wavelengths across the electromagnetic spectrum to determine light absorption by a material. The absorption characteristics are in response to at least two excitation light wavelengths. A light source is absorbed by molecules of a compound, causing little or no light from the light source to be reflected by the compound. The lack of reflected light from the light source by the material can be detected by one or more RGB sensors. The RGB sensors can be components of a broad-spectrum image sensor. The broad-spectrum sensor can employ an integrated, very low-cost Bayer filter, which enables the broad-spectrum image sensor to provide sensitivities to particular wavelengths, including light from frequencies which are visible to the human eye and those which are not. Various materials absorb different wavelengths of light when compared to one another. However, multispectral imaging can be used to differentiate materials based on their spectral absorption signatures and their absorption characteristics. As disclosed, multispectral absorption imaging can reduce the complexity, cost, and deployment challenges of using specialized multispectral cameras, elaborate optical filters, and expensive filter wheels which have orientation and alignment sensitivities, and employing fixed, lab-only equipment placement. The providing of excitation light wavelengths and the measuring output values of one or more RGB sensors can be performed by a mobile, outdoor-suitable vehicle. The mobile, outdoor-suitable vehicle can include a drone aircraft, an autonomous vehicle, and so on.

An absorption signal can be spectrally resolved using filters common to many color digital imagers, such as the Red, Green, and Blue Bayer filters integrated in typical, inexpensive RGB sensors that are the basis of common color digital imagers. These sensors generally demonstrate peak blue sensitivity at 400-475 nm, peak green sensitivity at 475-580 nm, and peak red sensitivity at 580-750 nm. Excitation sources at a wavelength near the edge of, or inside or outside of, the RGB visible light wavelength spectrum, which can be referred to as the extended RGB spectrum, can include wavelengths from 350 nm to 950 nm, for example. However, it should be noted that the definition of the exact wavelengths of visible light is somewhat subjective. For purposes of discussion, a visible light wavelength range of about 425 nm-725 nm is understood herein, although discrete wavelengths or wavelength ranges are used when possible. The excitation source wavelengths can, when used to illuminate a material sample, elicit an absorption response from the material sample that can be detected by an RGB sensor. That is, a given material sample will absorb, with varying magnitude, an impinging excitation source wavelength. The excitation source may be chosen to have a relatively narrow, non-overlapping excitation spectra to avoid "crosstalk" excitation.

Two RGB sensors can be employed to provide stereoscopic imaging. The stereoscopic imaging is valuable for feature detection, identification, and matching in a material sample. The two RGB sensors can have polarization filters inserted over or in front of them to provide a measure of polarization in the images. For example, one sensor can be "polarized" in a vertical direction, while the other sensor can be "polarized" in a horizontal direction, thus providing 90° "cross-polarization" for the stereoscopic imaging. This cross-polarization allows for the isolation of specularly reflected, polarized photons based on comparison of the images taken from the two sensors.

The low-cost, portable method of multispectral sample analysis disclosed herein uses an ordinary, readily available Red-Green-Blue (RGB) sensor. The RGB sensor typically is mass produced and has applications in low-cost technology that endeavors to detect light waves in the visible spectrum in a standard three-color, RGB palette suitable for digital processing. The RGB sensor typically employs an integrated Bayer filter applied during the manufacturing process of a CMOS, CCD, or similar sensor semiconductor fabrication. The Bayer filter is completely integrated in the sensor and cannot be removed, replaced, or adjusted. When light impinges the surface of an RGB sensor, the underlying photosensors register a signal related to the intensity of the impinging wavelengths as a function of the color of the integrated sensor directly over each photosensor device. The disclosed technology does not require expensive filter wheels, complex optical alignments, or stationary, non-handheld components.

FIG. 1 is a flow diagram for multispectral sample analysis using absorption signatures. Biochrome and/or water detection can be enabled by multispectral sample analysis. At least two excitation light wavelengths are provided to a material sample. The material sample exhibits absorption characteristics along the Red-Green-Blue (RGB) light wavelength spectrum. Output values of an RGB sensor are measured. The measuring detects the absorption characteristics of the material sample. The absorption characteristics are in response to the at least two excitation light wavelengths. An indication of composition of the material sample is generated. The indication is based on interpreting the output values that were measured.

The flow 100 includes providing an absorption excitation light wavelength 110 and a second absorption excitation light wavelength 112. The two excitation light wavelengths can provide information on absorption characteristics. The light wavelengths can be within the visible spectrum and/or outside of the visible spectrum. The flow 100 can include providing a further absorption excitation light wavelength 116. Each of the excitation wavelengths can provide a data point or points related to the absorption characteristics of the material sample (e.g., at least three data points, one for each excitation wavelength). The absorption characteristics can be ascertained by measuring the output values of an RGB sensor 120. Each output red, green, and blue of the RGB sensor provides a relative measurement of the material sample absorption while the material sample is irradiated with the excitation light wavelengths.

The flow 100 can include spacing the wavelengths of the excitations at least 100 nm apart 122. An excitation wavelength can be substantially at a certain wavelength when its spectral energy peak encompasses that wavelength within about 10% of the wavelength, due to real world implementations. This is illustrated by excitations 622, 624, and 626 of FIG. 6, for example. A useful excitation profile can show three excitations at substantially 523 nm, 660 nm, and 940 nm. The flow 100 includes enabling biochrome identification 130. As discussed later, a biochrome metric can be established based on the outputs of the RGB sensor as stimulated by the excitations. Biochromes such as collagen, fat, hemoglobin (Hgb), and oxygenated hemoglobin (oxyHgb), to name just a few, can be profiled and identified using biochrome metrics. For example, collagen can be identified by observing a monotonic decrease in fluorescence signal intensity in going from the blue to the green to the red channel of a RGB sensor in response to excitation with a blue or UV light source. Additionally, the absence or presence of relevant biochromes can be based on the presence of strong optical absorbers. For example, the strength of the reflected signal at a given wavelength relative to the strength of a signal reflected off a 95% reflective diffuse reflectance standard can provide biochrome identification. This comparison is performed for the red, green, and blue color channels typical of a color CMOS sensor.

The flow 100 includes enabling water identification 132. Unlike most biochromes, water exhibits a monotonically increasing absorption characteristic across an excitation profile as the excitation wavelength increases. Because water is such an integral component of living tissue, water identification can be very useful. Isolating water absorption can be performed by monitoring absorption at 800-1000 nm and comparing to absorption at longer wavelengths. Absorption by most chromophores found in nature decreases with increasing wavelength; however, in the case of water, the opposite is true. A light source with peak intensity from 800-1000 nm can be used to generate an absorption signal based on a comparison to a diffuse reflectance standard:

$$\text{Absorption Image} = -\log\left(\frac{(\text{Raw Image} - \text{Dark Image})/\text{Exp}}{(DR\ \text{Image} - \text{Dark Image})/\text{Exp}}\right)$$

where the raw image is the output of the RGB sensor with excitation light illumination as described herein, the dark image is the output of the RGB sensor with no excitation light illumination and only ambient lighting conditions, and the DR (diffuse reflectance) standard is a known and characterized sample that provides a baseline output of the RGB sensor with excitation light illumination.

Thus, a method for multispectral sample analysis is disclosed comprising: providing at least two excitation light wavelengths to a material sample, wherein the material sample exhibits absorption characteristics along the Red-Green-Blue (RGB) light wavelength spectrum; measuring output values of an RGB sensor, wherein the measuring detects the absorption characteristics of the material sample, and wherein the absorption characteristics are in response to the at least two excitation light wavelengths; and generating an indication of composition of the material sample, wherein the indication is based on interpreting the output values that were measured. Some embodiments include providing a third excitation light wavelength and measuring an additional output value of the RGB sensor. In embodiments, the at least two excitation light wavelengths and the third excitation light wavelength are wavelengths at least 100 nm apart from each other. In embodiments, the providing at least two excitation light wavelengths and the providing a third excitation light wavelength enables water identification. In embodiments, the water identification comprises identifying a predominately monotonically increasing absorption at longer wavelengths. Predominately monotonically can indicate at least an order of magnitude difference at two points. In embodiments, the providing at least two excitation light wavelengths and the providing a third excitation light wavelength enables biochrome identification. And some embodiments include providing at least one further additional excitation light wavelength and measuring a further additional output value of the RGB sensor.

The flow 100 includes using an additional, stereoscopic RGB sensor 134. The RGB sensor and the additional RGB sensor can provide a stereoscopic image of the material sample. Both the RGB sensor and the additional RGB sensor can be used with polarization 136. The RGB sensors can have polarization filters inserted over or in front of them to provide a measure of polarization in the images. For example, one sensor can be "polarized" in a vertical direction, while the other sensor can be "polarized" in a horizontal direction, thus providing 90° "cross-polarization" for the stereoscopic imaging. This cross-polarization allows for the isolation of singly scattered, polarized photons based on comparison of the images taken from the two sensors. Photons that undergo multiple scattering events deeper in the skin lose their polarization and contribute equally to the parallel and perpendicularly polarized signal. Deeper scattering tends to take place in, for example, the dermis, where randomly oriented collagen fibers primarily contribute to the loss of polarization. Thus, in embodiments, the polarization filters are rotated 90° in polarization with respect to each other, such that one of the polarization filters is oriented parallel to absorption photons and the other of the polarization filters is oriented perpendicularly to absorption photons.

The polarization filters can be chosen such that they lose their polarization effectiveness above a certain wavelength, for example, above a 700 nm wavelength. Thus, detecting polarized photons below a 700 nm wavelength and non-polarized photons above a 700 nm wavelength is enabled. In embodiments, the RGB sensor and the additional RGB sensor are each polarized using polarization filters. Some embodiments include feature matching of the material sample. For example, absorption images taken at 460 nm, 523 nm, and 660 nm when the left camera is polarized parallel to the LEDs and the right camera is polarized perpendicularly to the LEDs pose a problem: specular reflection features are not visible in both images. For stereomatching feature identification, the same features are required in both images. However, for wavelengths over the effective polarization wavelength of 700 nm (e.g., at 940 nm), features detectable in both sensors are the same. Thus, at 940 nm, the polarizers that sit in front of all of the LED's do not polarize the light and the specular reflections bleed through. Thus, feature mapping for the absorption case, that is, the photons that are not absorbed and are reflected back to the sensors, is enabled through the polarization filters. In embodiments, the polarization filters enable a depth of scattering analysis.

Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
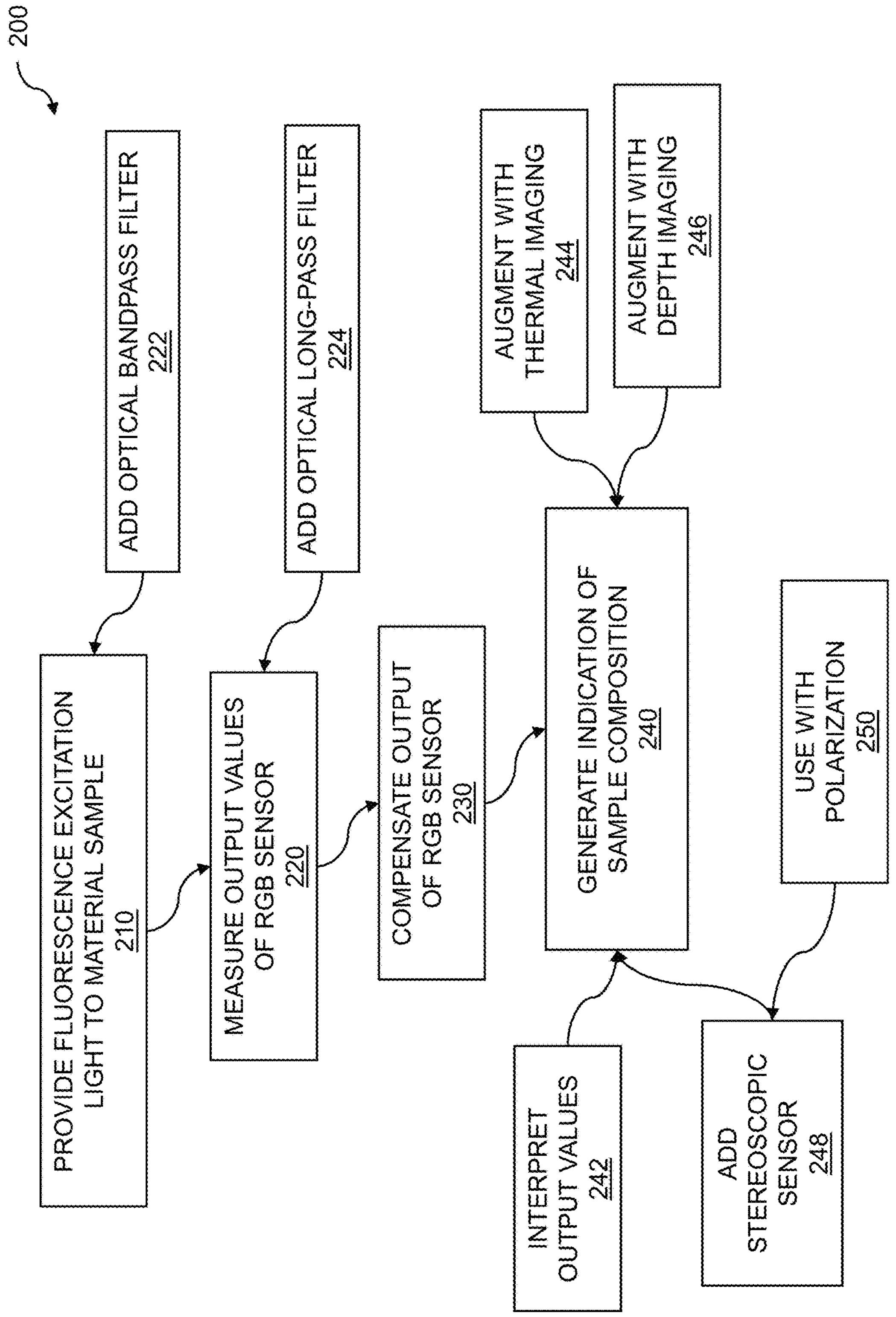
FIG. 2 is a flow diagram for multispectral sample analysis using fluorescence signatures.

FIG. 2 is a flow diagram for multispectral sample analysis using fluorescence signatures. At least one fluorescence excitation light wavelength is provided to a material sample. The material sample exhibits fluorescence characteristics along the Red-Green-Blue (RGB) light wavelength spectrum. Output values of an RGB sensor are measured. The measuring detects the fluorescence characteristics of the material sample in response to the at least one fluorescence excitation light wavelength. An indication of composition of the material sample is generated. The indication is based on interpreting the output values that were measured. Because no filter wheels are needed to filter the material sample fluorescence, and because the components can generally be obtained at low cost, the multispectral sample analysis techniques disclosed within can be implemented in a handheld unit.

The flow 200 includes providing a fluorescence excitation light to a material sample 210. The excitation light can emanate from a single source or from multiple sources, such as from an incandescent light source, an LED light source, a laser light source, an ultraviolet (UV) light source, an infrared (IR) light source, and so on. The excitation light wavelength can have a wavelength in the ultraviolet light region, which is less than a wavelength of an RGB light wavelength spectrum. The excitation light wavelength can be substantially between 200 nm and 450 nm. The excitation light of one or more wavelengths can illuminate a material sample, which can fluoresce in response. A common, inexpensive CMOS RGB sensor can measure the fluorescence amplitude according to the sensor's designed and manufactured wavelength response. The flow 200 includes measuring output values of an RGB sensor 220, in response to the excitation. The output values of the measured RGB light wavelengths are electrical signals, and thus the RGB sensor translates wavelength intensity to an electrical representation by providing three output values: a red output value, a green output value, and a blue output value. These sensors generally demonstrate peak blue sensitivity at 400-475 nm, peak green sensitivity at 475-580 nm, and peak red sensitivity at 580-750 nm. In order to avoid signal contribution from an excitation LED (or other excitation source) that has a long red tail which may be detected by the spectral channels built into the RGB imager, the excitation source may be outfitted with a bandpass filter that prevents crosstalk. Additionally, a long-pass filter placed in front of the RGB sensor further prevents a spurious signal from the excitation LED. In embodiments, at least one fluorescence excitation light wavelength signal comprises a wavelength less than a wavelength of the RGB light wavelength spectrum. And in embodiments, the wavelength, which is less than a wavelength of the RGB light wavelength spectrum, is substantially between 200 nm and 450 nm. A wavelength substantially between 200 nm and 450 nm can indicate that a high percentage of the excitation light energy, for instance at least 90%, is contained within the 200 nm to 450 nm wavelength region. The term "substantially" reflects an understanding that no real world, physically-based system can be described in exact terms, and therefore it is accurate and efficient to describe light wavelengths in a real system using "substantially" as a modifier.

The flow 200 can include adding an optical bandpass filter 222 between the excitation light and the material sample. A bandpass filter can prevent wavelengths of the excitation light from bleeding into the RGB sensor spectrum and contaminating the results. It should be understood that typical excitation sources will have a spectral energy curve centered at a given wavelength, but that there are usually energy tails at wavelengths other than those of the given wavelength. For example, an excitation source providing a nominal excitation wavelength at 405 nm may have an energy tail in the 1%-10% range at 450 nm, which would contaminate a measurement of an RGB sensor that is sensitive at 450 nm. Other sources, such as a laser excitation source, which are generally more expensive, may be able to provide a narrower wavelength spectrum. The bandpass filter can have a filter width dependent on its characteristics, cost, manufacturing tolerance, and so on. Some embodiments add an optical bandpass filter to at least one fluorescence excitation light wavelength to attenuate wavelengths of the fluorescence excitation light wavelength closest to the RGB light wavelength spectrum. In embodiments, the bandpass filter is centered at 400 nm. And in embodiments, the bandpass filter has a width of substantially 50 nm.

The flow 200 can include adding an optical long-pass filter 224 to the RGB sensor, that is, in between the material sample and the RGB sensor. A long-pass filter can block wavelengths below a cut-off wavelength and allow wavelengths above the cut-off wavelength. For example, a long-pass filter with a cut-off wavelength of 450 nm would prevent excitation wavelengths (e.g., at 405 nm) from contaminating a measurement of an RGB sensor that is sensitive below 450 nm. Of course, no filter is perfect, and the cut-off wavelength may not be a single, well-defined wavelength. Therefore, a bandpass filter and/or a long-pass filter may be used alone or together in order to provide a balance of cost, availability, size, portability, repeatability, etc. Some embodiments add an optical long-pass filter in front of the RGB sensor, which can prevent spurious signals from the excitation LED from reaching the RGB sensor. The long-pass filter is designed to cut off any wavelength which is near or less than a wavelength of the RGB light wavelength spectrum. In embodiments, the cut-off wavelength is substantially 30 nm greater than the at least one fluorescence excitation light wavelength. In embodiments, the long-pass filter has a cutoff wavelength less than a wavelength of the RGB light wavelength spectrum.

The flow 200 can include compensating the output of the RGB sensor 230. The compensating can involve providing a boost or attenuation to electrical output signals of the RGB sensor in order to counteract sensor differences, ambient lighting differences, excitation wavelength spectra differences, and so on. Because various RGB sensors can have various wavelength sensitivities and responses that may vary from sensor to sensor, or from manufacturing lot to manufacturing lot; or may fluctuate due to semiconductor aging, environmental conditions, and so on; compensating can be a key component in achieving sample identification precision. The compensating can be adjusted based on various calibration techniques that are performed before or after an actual sample measurement. Some embodiments compensate the output of the RGB sensor, based on an analysis of a wavelength response of the RGB sensor. In embodiments, the compensating identifies peak sensitivities for red, green, and blue sensing for the RGB sensor.

The flow 200 includes generating an indication composition of the material sample 240. The indication can be generated based on various techniques such as table lookup, graph comparison, machine learning, human interpretation, signature comparison, and the like. The indication can come from a library of RGB output sensor metrics, either compensated or uncompensated. The indication can be useful in many various endeavors as will be discussed shortly. The indication can be based on interpreting the output values 242 of the RGB sensor that were measured and compensated. The indication can be augmented with thermal imaging 244 or depth imaging 246. A multispectral sample analysis can combine the indication with thermal imaging and depth imaging via stereoscopy, LIDAR, Time of Flight, and so on, to determine how sample position in a scene determines signal intensity, which can subsequently be used to improve indication specificity. For example, if x is a distance between the sample and the RGB sensor, which could have integrated or discrete focusing lenses included, then to correct for photon density at x, the raw sample image at x can be compared to a diffuse reflectance standard at x. Some embodiments augment the generating with thermal imaging of the material sample. And some embodiments augment the generating with depth imaging of the material sample.

The flow 200 includes adding a stereoscopic sensor 248. An additional RGB sensor can be added to provide another angle from which an RGB sensor provides output. The additional RGB sensor enables stereoscopic imaging of the material sample. Output values of the additional RGB sensor can be used along with output values of the RGB sensor to indicate composition, determine features, compare features over time, and so on. Some embodiments include measuring output values of an additional RGB sensor, wherein the measuring detects the fluorescence characteristics of the material sample, and wherein the fluorescence characteristics are in response to the at least one fluorescence excitation light wavelength. In embodiments, the RGB sensor and the additional RGB sensor provide a left and a right stereoscopic sensor image.

The flow 200 includes using the RGB sensor and the additional RGB sensor with polarization 250. Polarization filters can be placed over, on, or in front of an RGB sensor to attenuate photon detection of one polarization, but to allow mostly unattenuated photon detection for another polarization. The polarization filters can be placed over the RGB sensors 90° out of phase with each other. Thus, one RGB sensor detects primarily "parallel" light wavelengths, and the other RGB sensor detects primarily "perpendicular" light wavelengths. The polarization filters can be chosen such that they lose their polarization effectiveness above a certain wavelength, for example, above a 700 nm wavelength. Thus, detecting polarized photons below a 700 nm wavelength and non-polarized photons above a 700 nm wavelength is enabled. In embodiments, the RGB sensor and the additional RGB sensor are each polarized using polarization filters. Some embodiments include feature matching of the material sample. For fluorescence photons, which are not inherently polarized as emitted from the material sample, and for wavelengths over the effective polarization wavelength of 700 nm (e.g., at 940 nm), features detectable in both sensors are the same. Thus, at 940 nm, the polarizers that sit in front of all of the LED's do not polarize the light and as a result, the specular reflections bleed through. And in the case of fluorescence photons, which are not polarized, there is no specular reflection. Thus, feature mapping for fluorescence photons is enabled through the polarization filters.

Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
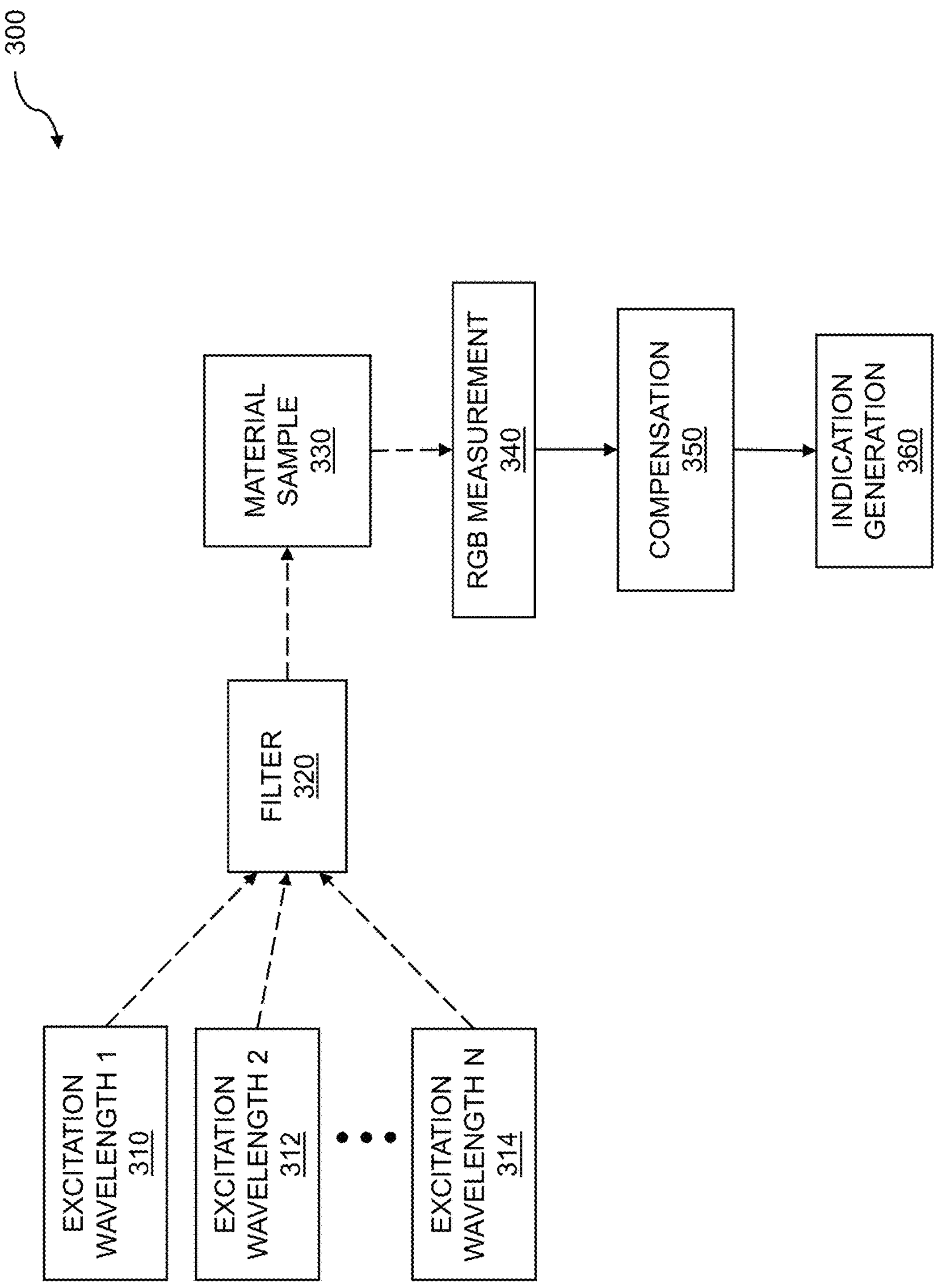
FIG. 3 shows a system block diagram for multispectral sample analysis.

FIG. 3 shows a system block diagram for multispectral sample analysis. In the system block diagram 300, one or more absorption excitation light wavelengths are provided to a material sample, such as excitation wavelength 1 310, excitation wavelength 2 312, up to excitation wavelength N 314. The excitation wavelengths can emanate from a single source or from multiple sources, such as from an incandescent light source, an LED light source, a laser light source, an ultraviolet (UV) light source, an infrared (IR) light source, and so on. The excitation wavelengths can illuminate a sample, and the resulting absorption signature can be measured. The system block diagram illustrates multispectral sample analysis using absorption signatures. At least two excitation light wavelengths are provided to a material sample. The sample exhibits absorption characteristics along the Red-Green-Blue (RGB) light wavelength spectrum. Output values of an RGB sensor are measured. The measuring detects the absorption characteristics of the sample. The absorption characteristics are in response to the at least two excitation light wavelengths. A third excitation light wavelength is provided and an additional output value of the RGB sensor is measured. The providing at least two excitation light wavelengths and a third excitation light wavelength enable water identification and biochrome identification. An indication of composition of the material sample is generated. The indication is based on interpreting the output values that were measured. An additional RGB sensor enables stereoscopic sensor imaging.

The system block diagram 300 can include one or more optical filters 320 on the source side of a material sample 330. That is, the one or more excitation wavelengths 310, 312, and 314 can be conditioned by the one or more optical filters 320 such that the illuminating light from the excitation wavelengths is affected by the filters before it reaches the material sample 330. These filters do not affect the fluorescence emissions of the material sample that are detected by an RGB sensor, based on the stimulation of the one or more excitation wavelengths. The filter 320 can be a bandpass filter. The one or more excitation wavelengths, as conditioned by any intervening filters 320, then impinge on a material sample 330, resulting in a fluorescence emission from the sample that is detected by RGB measurement block 340. Note that before RGB measurement block 340, the system block diagram 300 indicates light transmission, as denoted by the dashed lines among blocks 310, 312, 314, 320, 330, and 340. The output of RGB measurement block 340, as well as the signals between subsequent blocks 350 and 360, are electrical signals, as denoted by the solid lines. Optionally, an additional optical filter (not shown) can be placed between the material sample 330 and the RGB measurement 340. The additional optical filter can be a long-pass filter.

The electrical output of RGB measurement block 340 can be compensated by compensation block 350. Compensation can involve providing a boost or attenuation to electrical signals indicating a certain magnitude of a particular light wavelength in order to counteract sensor differences, ambient lighting differences, excitation wavelength spectra differences, and so on. The compensation block 350 can be adjusted based on various calibration techniques that are performed before or after an actual sample measurement. The output of compensation block 350 can enable generation of an indication 360 of a composition of a material sample. Analysis of the output of compensation block 350 (or directly from RGB measurement block 340) can enable generation of an indication of composition, based on the output of block 350 (or directly from block 340) using various methods such as table lookup, graph comparison, machine learning, human interpretation, signature comparison, and the like.

Figure 4:
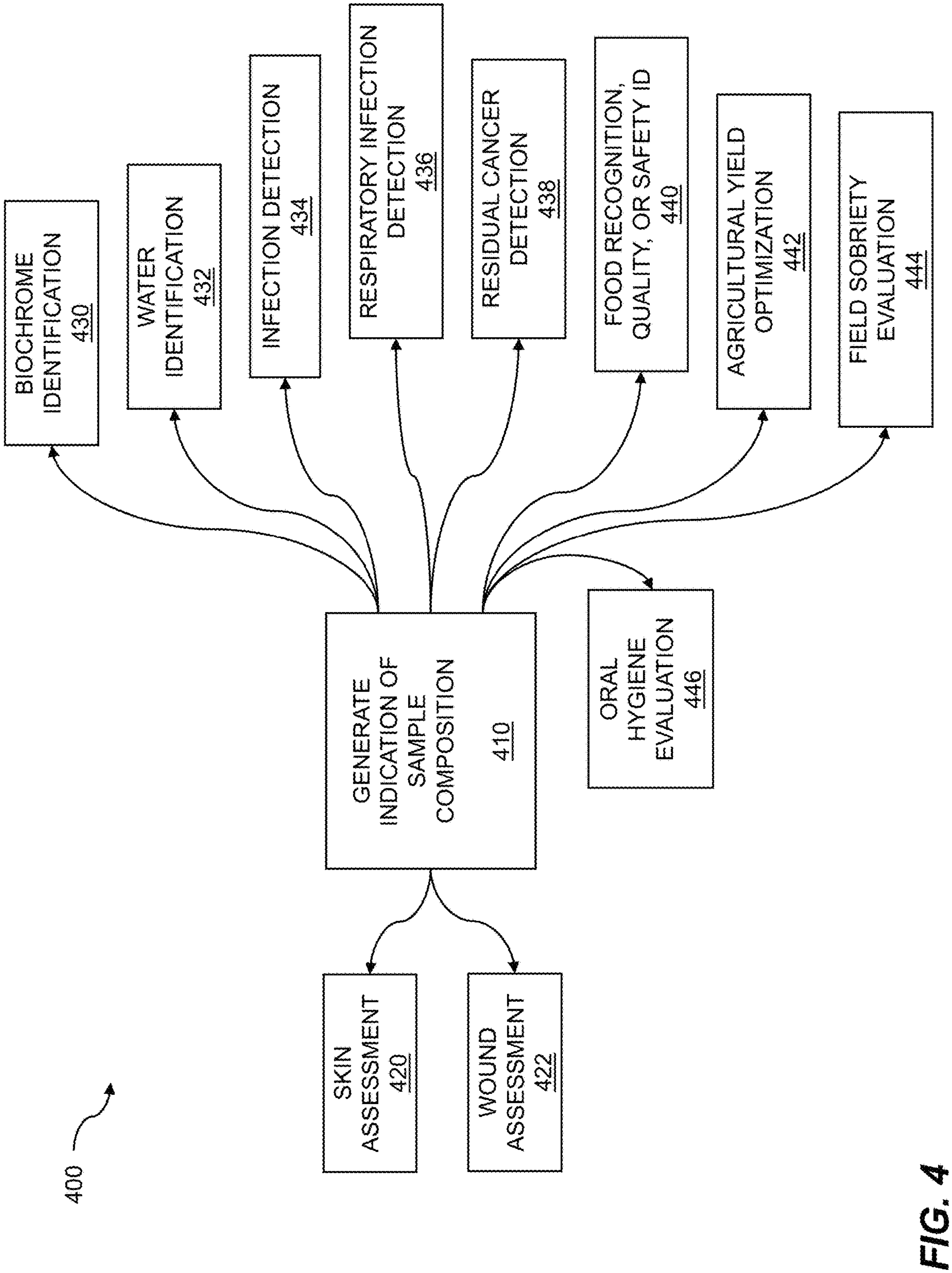
FIG. 4 shows a system block diagram for using fluorescence signatures.

FIG. 4 shows a system block diagram for using absorption signatures. Absorption signatures can enable multispectral sample analysis by generating an indication of sample composition. An indication of sample composition can be useful in a variety of human endeavors, as will be discussed below. The block diagram 400 can include generating an indication of sample composition 410. As discussed throughout, at least two excitation light wavelengths are provided to a material sample. The sample exhibits absorption characteristics along the Red-Green-Blue (RGB) light wavelength spectrum. Output values of an RGB sensor are measured. The measuring detects the absorption characteristics of the sample. The absorption characteristics are in response to the at least two excitation light wavelengths. A third excitation light wavelength is provided and an additional output value of the RGB sensor is measured. The providing at least two excitation light wavelengths and a third excitation light wavelength enable water identification and biochrome identification. An indication of composition of the material sample is generated. The indication is based on interpreting the output values that were measured. An additional RGB sensor enables stereoscopic sensor imaging.

The indication can enable skin assessment 420. The skin assessment can involve predicting the onset of skin conditions such as psoriasis, which can be distinguished based on fluorescence from fluorophores such as melanin, elastin, collagen, keratin, and flavoprotein. Other skin conditions, such as eczema and acne, can also be predicted. In addition, skin hydration can be assessed using the disclosed techniques. The skin assessment can include feature identification. The indication can enable wound assessment 422. The wound assessment can be based on collecting a variety of images at different excitation wavelengths and spatially registering the images using micro- or macro-scale features, skin and wound edges, fiducial marks, reference standards for alignment, corresponding biological features, and the like. Feature recognition can be accomplished using Laplace of Gaussians, difference of Gaussians, Hessian-Laplace, scale invariant feature transform (SIFT), multi-scale-oriented patches (MOPS), or other image processing techniques for local feature description. Once corresponding features on images are identified, the registration technique can use translation, rigid body, rotation, or affine transformation methods to register multiple images collected at different wavelengths. A pixel-by-pixel registration allows for the images to be digitally processed in order to identify biological features, to perform calculations which isolate or enhance the biological signals, and/or to assess wound healing. Further analysis can enable algorithmic identification of infection. In embodiments, the wound assessment includes infection detection. In embodiments, the skin assessment includes wound assessment. In embodiments, the wound assessment is taken over time. In embodiments, the wound assessment is repeated over time and enables a wound care treatment plan. In embodiments, the skin assessment is updated using temporal change feature matching, that is, by comparing identified features in the wound to determine how they are changing temporally (i.e., with the passage of time). The temporal change can occur over two or more healthcare clinical sessions. At least one of the two or more healthcare clinical sessions can be self-administered.

As discussed previously, the indication can enable biochrome identification 430 and water identification 432. In addition, the indication can enable infection detection 434 or respiratory infection detection 436. Host metabolism plays a vital role in viral infections. Energy yielding metabolic pathways are repurposed by the virus to support viral replication. High concentrations of nicotinamide adenine dinucleotide+hydrogen (NADH) and flavins are indicative of such infections. The indication can be generated by isolating signals from NADH and flavins by collecting fluorescence photons in the R, G, and B channels, respectively, and exciting at or near 400 nm. This approach further isolates features in an image that can be attributed to the presence of flavins and NADH by taking the normalized ratio, where normalization is based on excitation flux, integration time, and channel sensitivity of the green channel signal to the blue channel signal, and isolating based on pixels that yield a ratio value indicative of the presence of NADH and/or flavins.

In addition, abnormal concentrations of porphyrin, which can be detected using the disclosed concepts, have been observed in serum from COVID-19 patients. Other respiratory related infections, such as sinusitis, are more prevalent with a common cold than with influenza. These infections can be analyzed based on the fact that signatures of sinusitis, such as fluid in the sinuses, can increase the indication precision to distinguish between respiratory infection types. Furthermore, common cold viruses usually do not cause substantial damage to the airway epithelium, whereas influenza and COVID-19 can damage cells in the respiratory epithelium. In fact, a broad variety of respiratory pathogens, including rhinoviruses, coronaviruses, and the like, can adversely affect cells. Redness and inflammation associated with such cellular damage can be detected using the disclosed techniques. By applying the disclosed techniques when looking into a patient's throat and taking images to measure fluorescence, absorption and thermal radiation from the throats of patients with possible infection from respiratory viruses such as SARS-CoV-2, Influenza A and Influenza B can be detected. Such methods can also facilitate telemedicine diagnostics. In embodiments, the indication enables infection detection. In embodiments, the infection detection is based on biochrome identification. In embodiments, the indication enables respiratory infection detection. In embodiments, the respiratory infection detection comprises influenza detection. In embodiments, the influenza detection comprises COVID-19 detection.

This technology isolates signals from infection-associated biochromes, such as Porphyrin and Pyoverdine, by holding an excitation wavelength constant and collecting signals from progressively longer wavelength emission channels. This action is performed at each pixel in an image. In one embodiment, fluorescence is collected by exciting wavelengths in the blue/UV region of the spectrum such that the peak of the spectral distribution of the excitation source is at a lower wavelength (higher energy) than what is typically detected by the sensor (CMOS or CCD as examples) that is being used for detecting photons and generating an image.

The indication can enable residual cancer detection 438. Autofluorescence imaging is enabled by the disclosed concepts and has been used to diagnose oral cancer, breast cancer, lung cancer, skin cancer, brain cancer, and others. Autofluorescence from NADH has been cited as one possible biomarker for targeting cancer. Similarly, fluorescence from dense connective tissue (extracellular matrix, etc.) associated with tumor can be used to delineate tumor boundaries. In addition, such techniques can enable detection of residual cancer during surgery. In embodiments, the indication enables residual cancer detection. In further embodiments, the residual cancer detection occurs during oncological surgery.

The indication can enable food recognition, food quality, or food safety 440. Common food borne pathogens include *E. coli, Salmonella, Listeria, Cyclospora*, and Hepatitis A. Disclosed techniques can enable rapid detection of food borne pathogens in order to avoid distribution of contaminated foods. Authentication, quality, and possible adulteration of food must be monitored for distribution and consumption. For example, liquor, wine, and beer inspection can be performed by analyzing both water content and the presence of fluorescent compounds. Fluorescent compounds such as polyphenols, flavonoids, stilbenes, tannins, coumarins, and fluorescent amino acids are key markers of authenticity and quality. In some embodiments, two or three excitation LEDs at different blue and UV wavelengths may be employed for determining a shift in emission resulting from a change in excitation frequency. Such techniques can be used in plant food quality analysis, milk quality analysis, fruit quality analysis, coffee quality analysis, as well a protein quality analysis of products as varied as beef and sashimi, to name just a few. Other applications include monitoring the progress of fermentation, such as malolactic fermentation, for the deacidification of red wines. In-line monitoring of the fermentation process can also be applied to fermentation processes in which yeast or bacteria are programmed to produce a specific chemical such as THC and CBD. In addition, monitoring caloric intake can be enabled by food composition and rough, overall portion size identification. In embodiments, the indication of composition of the material sample includes identification of the presence of water, and the presence of water is used to determine organism health for the material sample. In embodiments, the indication enables food recognition, food quality, or food safety identification. In embodiments, the food quality detects food adulteration. And in embodiments, the food quality monitors progression of fermentation.

The indication can enable agricultural yield optimization 442. Especially in automated indoor farming, which is poised to assume a significant burden of the food supply, the disclosed techniques can enable identification of crop ripeness, crop water sufficiency, crop fertilization sufficiency, crop disease detection, and so on. This approach can enable minimized use of insecticides and herbicides while optimizing crop yield. In addition, a robot- or drone-based approach to agricultural optimization is feasible due to the portable attributes of the disclosed techniques. In embodiments, the indication enables agricultural yield optimization. In embodiments, providing excitation and measuring RGB sensor output values are accomplished using drone technology. The indication can have applications in law enforcement and can enable a field sobriety evaluation 444 for an individual. A contactless evaluation using the disclosed techniques can determine the need for a more invasive breathalyzer test. In addition to visual indicators such as enlarged pupils and eye movement that is faster than normal, measured amounts of vasoconstriction and vasodilation, depending on a level of intoxication, can be enabled using the indication. In embodiments, the indication enables field sobriety evaluation of individuals. In embodiments, the field sobriety evaluation of individuals is accomplished in a contactless manner. The indication can have further applications in dental care. The indication can enable an oral hygiene evaluation 446 for an individual. This can include detecting plaque, gingivitis, and other dental abnormalities using multispectral imaging and fluorescence. Thus, in embodiments, the indication enables oral hygiene evaluation.

Figure 5:
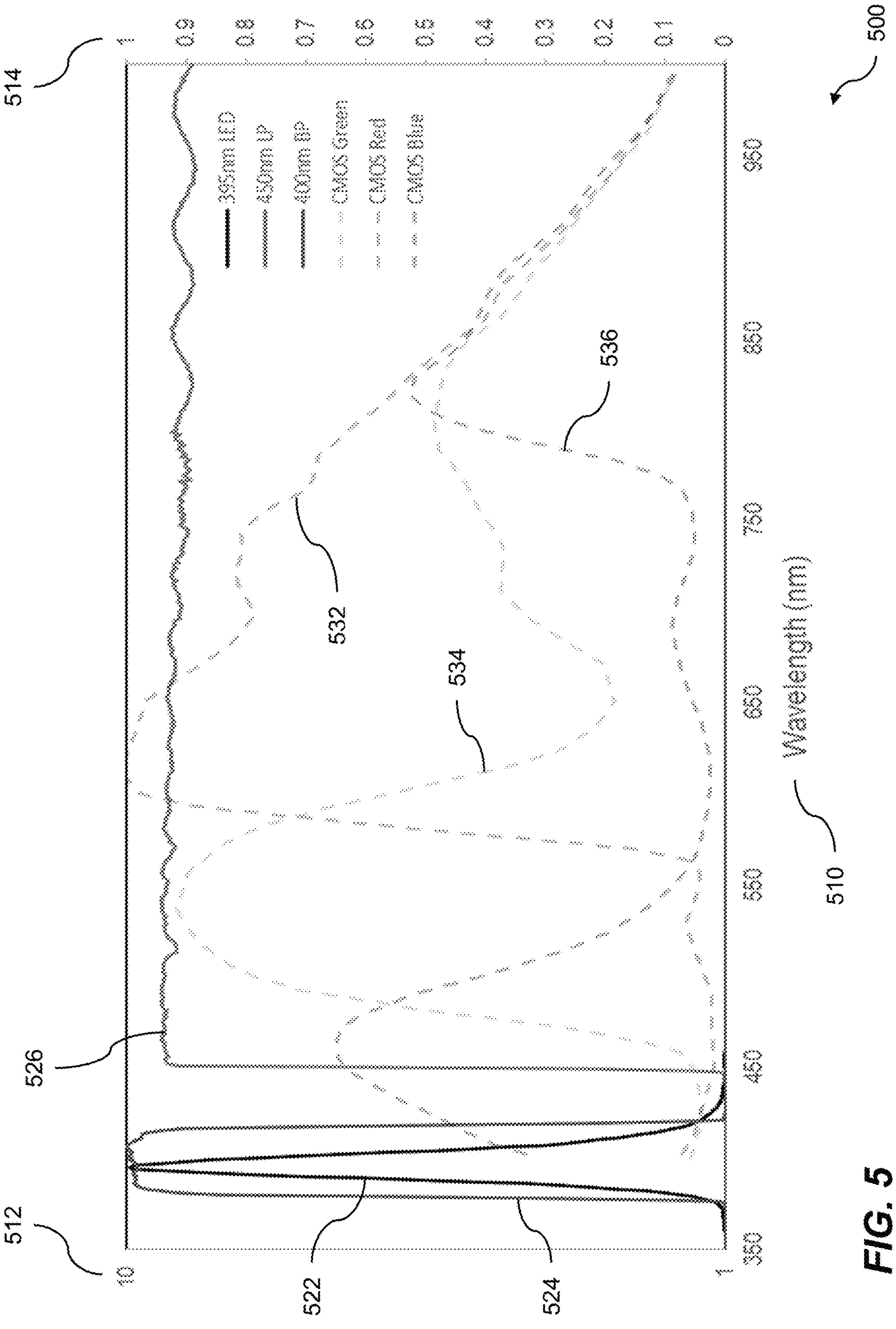
FIG. 5 is a graph showing fluorescence measurements.

FIG. 5 is a graph showing fluorescence measurements. Fluorescence measurements can be useful in understanding the indication of composition of a material sample. Various material samples, such as living organism samples, tissue samples, blood samples, skin samples, wound samples, infection samples, food samples, dental or oral hygiene samples, inanimate object samples, and so on can have fluorescence measurements performed on them. For fluorescence measurements, at least one fluorescence excitation light wavelength is provided to a material sample. The material sample exhibits fluorescence characteristics along the Red-Green-Blue (RGB) light wavelength spectrum. Output values of an RGB sensor are measured. The measuring detects the fluorescence characteristics of the material sample in response to the at least one fluorescence excitation light wavelength. An indication of composition of the material sample is generated. The indication is based on interpreting the output values that were measured.

In the graph 500, an x-axis indicating wavelength 510 is provided. Increasing wavelength from left to right indicates decreasing frequency of light waves and a traversal from the ultraviolet spectrum, roughly sub-400 nm, through the blue, green, and red wavelength regions, roughly 450 nm, 550 nm, and 650 nm, respectively, to the infrared wavelength band, which is roughly greater than 750 nm. It should be noted that an exact wavelength definition of a particular color is somewhat arbitrary and dependent on the sensor type. For example, the cones of a human eye roughly sense RGB signals using three cone types, but they are generally distributed differently from a typical CMOS RGB sensor's output. However, maintaining a consistent definition for a given system is generally required in order to provide consistent sample indications. The graph 500 also includes a left y-axis of absorption amount 512 from one to ten and a right y-axis of transmission amount 514 from zero to one.

The graph 500 includes excitation wavelength 522. The excitation wavelength 522 is centered substantially at 405 nm in the ultraviolet light wavelength spectrum. Note that wavelength 522 is a relatively narrow excitation, but that due to practical considerations, energy tails of the excitation wavelength can sometimes extend up toward the visible light RGB spectrum at 450 nm and above. To prevent bleed-over into the RGB spectrum, a bandpass filter, indicated by transmission spectrum 524, can be included. The bandpass filter can help attenuate excitation wavelengths outside of the band, such as a 50 nm bandpass filter centered at 400 nm. To further prevent bleed-over into the RGB spectrum, a long-pass filter, indicated by absorption spectrum 526, can be included. It should be noted that the bandpass optical filters can be placed between an excitation source and a sample, and the long-pass optical filter can be placed between the sample and an RGB sensor. In this manner, the excitation wavelength does not "bleed over" and affect the fluorescence measurements of wavelengths being emitted by the stimulated sample.

The graph 500 includes RGB sensor characteristics, such as sensor characteristic 532, indicative of the "R" or red output of an RGB sensor, sensor characteristic 534, indicative of the "G" or green output of an RGB sensor, and sensor characteristic 536, indicative of the "B" or blue output of an RGB sensor. The RGB outputs represented by characteristics 532, 534, and 536 can be used directly or can be compensated (as discussed elsewhere) to enable generation of an indication of material composition.

Figure 6:
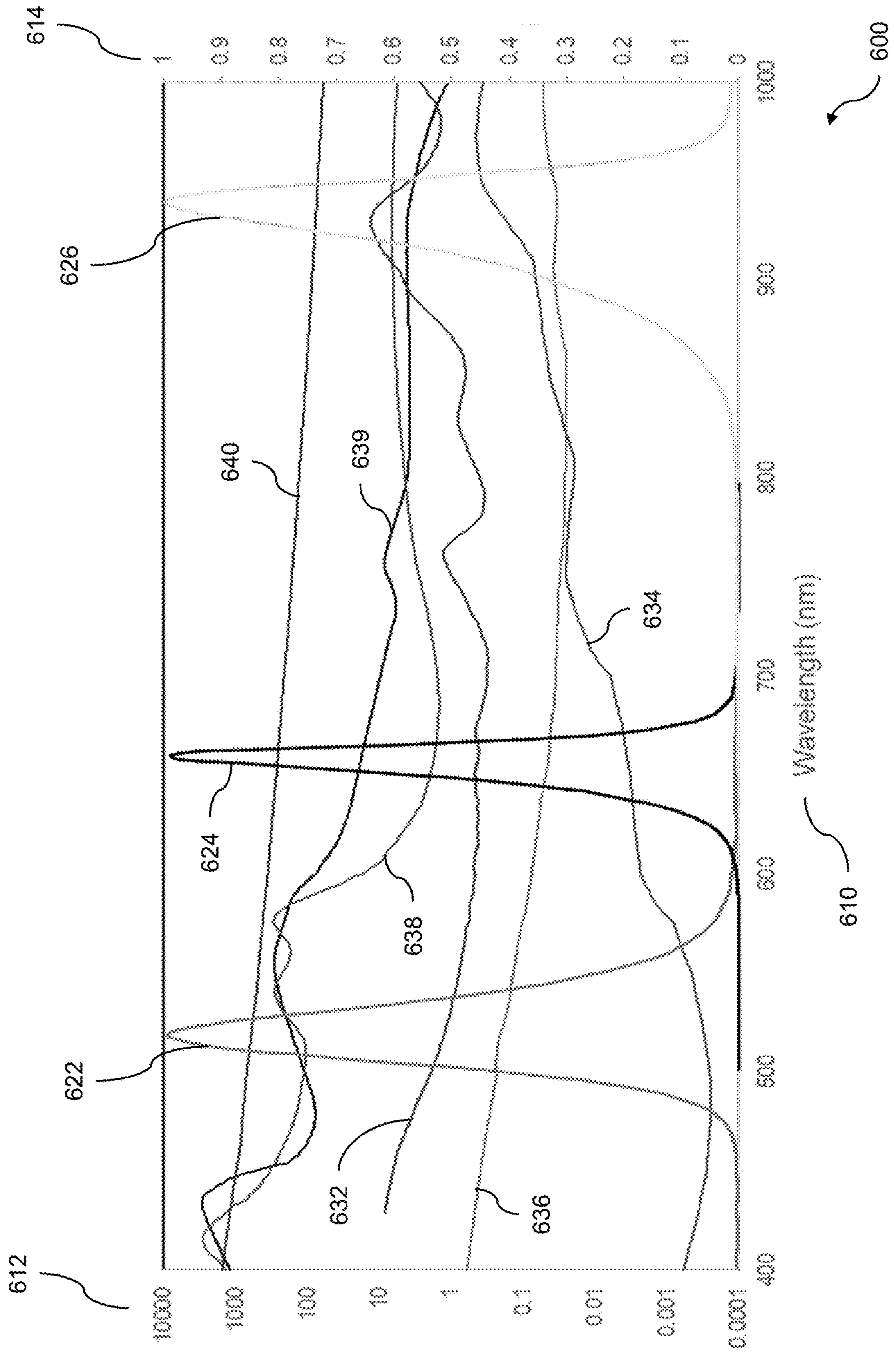
FIG. 6 is a graph illustrating biochrome and water absorption.

FIG. 6 is a graph illustrating biochrome absorption and water absorption. Absorption characteristics can be useful in understanding the identification of biochromes and water in a living organism sample. In the graph 600, an x-axis indicating wavelength 610 is provided. Increasing wavelength from left to right indicates decreasing frequency of light waves and a traversal from the ultraviolet spectrum, roughly sub-400 nm, through the blue, green, and red wavelength regions, roughly 450 nm, 550 nm, and 650 nm, respectively, to the infrared band, which is roughly greater than 750 nm. It should be noted that an exact wavelength definition of a particular color is somewhat arbitrary and dependent on the sensor type. For example, the cones of a human eye roughly sense RGB signals using three cone types, but they are generally distributed differently from a typical CMOS RGB sensor's output. However, maintaining a consistent definition for a given system is generally required in order to provide consistent sample indications. The graph 600 also includes a logarithmic left y-axis of absorption 612 and a linear right y-axis of normalized excitation 614.

The graph 600 illustrates three excitation wavelengths for sample illumination. Excitation wavelength 622 is substantially centered at a wavelength of about 523 nm; excitation wavelength 624 is substantially centered at a wavelength of about 660 nm; and excitation wavelength 626 is substantially centered at a wavelength of about 940 nm. Thus, the three excitation wavelengths, wavelength 622, wavelength 624, and wavelength 626, are spaced at least 100 nm apart over an extended visible light spectrum. The sharp, bell curve shape of the excitations provides for little to no overlap of those excitation wavelengths. Also, it can be noted that 940 nm light is sometimes considered to be near-infrared (NIR) wavelength light. However, most silicon-based CMOS sensors detect 940 nm light. In some usage scenarios, a short-pass filter is applied to prevent noise from NIR photons if that wavelength is not being used by an application. Nonetheless, a 940 nm wavelength can be considered part of an extended visible light spectrum and included when discussing RGB sensor usage.

The graph 600 includes various biochrome and water absorption characteristics, such as a hemoglobin (Hgb) absorption characteristic 632 and a water absorption characteristic 634. By taking the value of each absorption characteristic line on graph 600 at each of the three excitation wavelengths 622, 624, and 626, a tri-valued metric can be determined. Notably, while many of the biochrome absorption characteristics wander about with no simple trend across increasing wavelength, such as is observed for Hgb absorption characteristic 632, the water absorption characteristic 634 displays a monotonically increasing metric across increasing wavelength excitations 622, 624, and 626, which metric increases close to three orders of magnitude across the excitations.

The graph 600 shows other absorption characteristics, such as melanin absorption characteristic 640, fat absorption characteristic 639, oxygenated hemoglobin (oxyHgb) absorption characteristic 638, and collagen absorption characteristic 636. The graph 600 thus illustrates a method for multispectral sample analysis comprising: providing at least two excitation light wavelengths to a material sample, wherein the material sample exhibits absorption characteristics along the Red-Green-Blue (RGB) light wavelength spectrum; measuring output values of an RGB sensor, wherein the measuring detects the absorption characteristics of the material sample, and wherein the absorption characteristics are in response to the at least two excitation light wavelengths; and generating an indication of composition of the material sample, wherein the indication is based on interpreting the output values that were measured.

Figure 7:
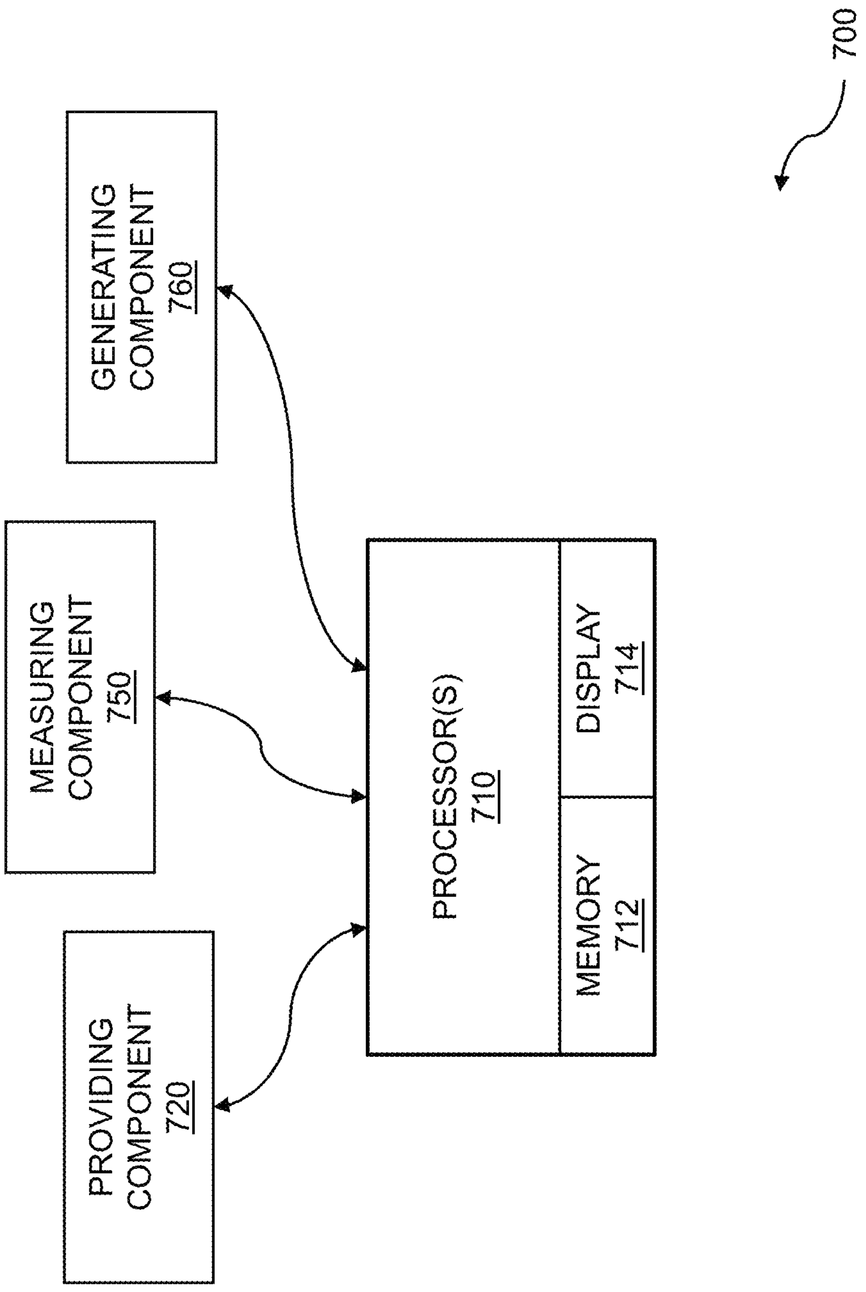
FIG. 7 is a system diagram for multispectral sample analysis using an absorption signature.

FIG. 7 is a system diagram for multispectral sample analysis using an absorption signature. The system 700 can include one or more processors 710, which are attached to a memory 712 which stores instructions. The system 700 can further include a display 714 coupled to the one or more processors 710 for displaying data, indications of sample analysis, directions, input requests, control options, excitation wavelengths, filter options, compensation options, data forwarding options, and so on. Embodiments of the system 700 comprise a computer system for multispectral sample analysis comprising: one or more processors 710 that are coupled to the memory 712 which stores instructions, wherein the one or more processors, when executing the instructions which are stored, are configured to: provide at least two excitation light wavelengths to a material sample, wherein the material sample exhibits absorption characteristics along the Red-Green-Blue (RGB) light wavelength spectrum; measure output values of an RGB sensor, wherein the measuring detects the absorption characteristics of the material sample, and wherein the absorption characteristics are in response to the at least two excitation light wavelengths; and generate an indication of composition of the material sample, wherein the indication is based on interpreting the output values that were measured.

The system 700 can include a providing component 720. The providing component 720 can be used to provide light excitation wavelengths directed toward a material sample undergoing analysis. The light excitation provided can come from various different sources including an incandescent light source, an LED light source, a laser light source, and so on. The light source or sources can emit a narrow spectrum of light at primarily one wavelength, at primarily two or more wavelengths, across a broad spectrum of multiple wavelengths, in the visible spectrum, in the infrared spectrum, in the ultraviolet spectrum, and so on. The excitation wavelengths can be targeted towards material sample fluorescence or material sample absorption. An absorption excitation light wavelength signal can have a wavelength within an extended RGB light wavelength spectrum. Excitation wavelengths of 523 nm, 660 nm, and 940 nm can be provided, for example.

The system 700 can include a measuring component 750. The measuring component 750 can provide a digital or analog signal output related to the magnitude of incoming light wavelengths from a sample. The measuring component 750 can comprise an RGB sensor. The output from the RGB sensor of the measuring component can be processed using various signal processing techniques. For example, the measuring component output can be compensated to account for naturally occurring manufacturing differences in the RGB sensor by completing a calibration step before the material sample is analyzed.

The system 700 can include a generating component 760. The generating component 760 can provide analysis of the RGB sensor output from the measuring component 750 to provide indication of composition of the material sample, based on interpreting the output values that were measured. The interpreting the output values to provide indication of composition can be performed using various methods such as table lookup, graph comparison, machine learning, human interpretation, signature comparison, and the like. The indication of composition can be useful for enabling medical evaluation such as skin assessment; wound assessment; wound assessment over time; treatment planning for wound care; infection detection; biochrome identification; respiratory infection detection; influenza detection; COVID-19 detection; residual cancer detection; oncological surgery residual cancer detection; oral hygiene detection such as detecting plaque, gingivitis, and other dental abnormalities; and so on. Further, the indication of composition can have applications in food recognition, food quality assessment, or food safety evaluation, detecting food adulteration, monitoring progression of fermentation, optimizing agricultural yield, and enabling field sobriety evaluation of individuals, to name just a few.

The system 700 can include a computer program product embodied in a non-transitory computer readable medium for multispectral sample analysis, the computer program product comprising code which causes one or more processors to perform operations of: providing at least two excitation light wavelengths to a material sample, wherein the material sample exhibits absorption characteristics along the Red-Green-Blue (RGB) light wavelength spectrum; measuring output values of an RGB sensor, wherein the measuring detects the absorption characteristics of the material sample, and wherein the absorption characteristics are in response to the at least two excitation light wavelengths; and generating an indication of composition of the material sample, wherein the indication is based on interpreting the output values that were measured.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general-purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited to neither conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A method for multispectral sample analysis comprising:

providing at least two excitation light wavelengths to a material sample, wherein the material sample exhibits absorption characteristics along the Red-Green-Blue (RGB) light wavelength spectrum;

measuring output values of an RGB sensor and an additional RGB sensor, wherein the RGB sensor and the additional RGB sensor are each polarized using polarization filters in front of the RGB sensors, wherein the measuring detects the absorption characteristics of the material sample, and wherein the absorption characteristics are in response to the at least two excitation light wavelengths, wherein a first excitation wavelength selected from the at least two excitation wavelengths is below an effective polarization wavelength corresponding to the polarization filters, such that the first excitation wavelength is polarized, and wherein a second excitation wavelength selected from the at least two excitation wavelengths is above the effective polarization wavelength, such that the second excitation wavelength is not polarized; and generating an indication of composition of the material sample, wherein the indication is based on interpreting the output values that were measured.

2. The method of claim 1 further comprising providing a third excitation light wavelength and measuring an additional output value of the RGB sensor.

3. The method of claim 2 wherein the at least two excitation light wavelengths and the third excitation light wavelength are at least 100 nm apart from each other.

4. The method of claim 3 wherein the providing at least two excitation light wavelengths and the providing a third excitation light wavelength enable water identification.

5. The method of claim 4 wherein the water identification comprises identifying a predominately monotonically increasing absorption at longer wavelengths.

6. The method of claim 2 wherein the providing at least two excitation light wavelengths and the providing a third excitation light wavelength enables biochrome identification.

7. The method of claim 2 further comprising providing at least one further additional excitation light wavelength and measuring a further additional output value of the RGB sensor.

8. The method of claim 1 wherein the measuring detects the absorption characteristics of the material sample, and wherein the absorption characteristics are in response to the at least two excitation light wavelengths.

9. The method of claim 8 wherein the RGB sensor and the additional RGB sensor provide a left and a right stereoscopic sensor image.

10. The method of claim 1 wherein the polarization filters are rotated 90° in polarization with respect to each other.

11. The method of claim 1 wherein one of the polarization filters is oriented parallel to absorption photons and the other of the polarization filters is oriented perpendicularly to absorption photons.

12. The method of claim 1 wherein the polarization filters provide polarization below a 700 nm wavelength.

13. The method of claim 12 further comprising using a light wavelength greater than the 700 nm wavelength for feature matching of the material sample.

14. The method of claim 13 wherein the feature matching of the material sample is enabled by a wavelength of light that is non-polarized.

15. The method of claim 14 wherein the wavelength of light that is non-polarized is 940 nm light.

16. The method of claim 1 wherein the polarization filters enable a depth of scattering analysis.

17. The method of claim 1 wherein the indication of composition of the material sample includes identification of the presence of water.

18. The method of claim 17 wherein the presence of water is used to determine organism health for the material sample.

19. The method of claim 1 wherein the providing and the measuring are performed by a mobile, outdoor-suitable vehicle.

20. The method of claim 19 wherein the mobile, outdoor-suitable vehicle is a drone aircraft.

21. The method of claim 1 wherein the indication enables a skin assessment.

22. The method of claim 1 wherein the indication enables a wound assessment.

23. The method of claim 22 wherein the wound assessment is repeated over time and enables a wound care treatment plan.

24. The method of claim 1 wherein excitation sources for the at least two excitation light wavelengths have non-overlapping excitation spectra.

25. The method of claim 1 further comprising adding an optical long-pass filter in front of the RGB sensor.

26. The method of claim 25 wherein the optical long-pass filter prevents spurious signals from reaching the RGB sensor.

27. A computer program product embodied in a non-transitory computer readable medium for multispectral sample analysis, the computer program product comprising code which causes one or more processors to perform operations of:

providing at least two excitation light wavelengths to a material sample, wherein the material sample exhibits absorption characteristics along the Red-Green-Blue (RGB) light wavelength spectrum;

measuring output values of an RGB sensor and an additional RGB sensor, wherein the RGB sensor and the additional RGB sensor are each polarized using polarization filters in front of the RGB sensors, wherein the measuring detects the absorption characteristics of the material sample, and wherein the absorption characteristics are in response to the at least two excitation light wavelengths, wherein a first excitation wavelength selected from the at least two excitation wavelengths is below an effective polarization wavelength corresponding to the polarization filters, such that the first excitation wavelength is polarized, and wherein a second excitation wavelength selected from the at least two excitation wavelengths is above the effective polarization wavelength, such that the second excitation wavelength is not polarized; and generating an indication of composition of the material sample, wherein the indication is based on interpreting the output values that were measured.

28. A computer system for multispectral sample analysis comprising:

a memory which stores instructions;

one or more processors coupled to the memory wherein the one or more processors, when executing the instructions which are stored, are configured to:

provide at least two excitation light wavelengths to a material sample, wherein the material sample exhibits absorption characteristics along the Red-Green-Blue (RGB) light wavelength spectrum;

measure output values of an RGB sensor and an additional RGB sensor, wherein the RGB sensor and the additional RGB sensor are each polarized using polarization filters in front of the RGB sensors, wherein the measuring detects the absorption characteristics of the material sample, and wherein the absorption characteristics are in response to the at least two excitation light wavelengths, wherein a first excitation wavelength selected from the at least two excitation wavelengths is below an effective polarization wavelength corresponding to the polarization filters, such that the first excitation wavelength is polarized, and wherein a second excitation wavelength selected from the at least two excitation wavelengths is above the effective polarization wavelength, such that the second excitation wavelength is not polarized; and generate an indication of composition of the material sample, wherein the indication is based on interpreting the output values that were measured.

* * * * *